(12) United States Patent
Kivi et al.

(10) Patent No.: US 11,684,295 B2
(45) Date of Patent: Jun. 27, 2023

(54) SAFE AND RELIABLE TRANSABDOMINAL FETAL OXIMETRY

(71) Applicant: Storx Technologies, Inc., Davis, CA (US)

(72) Inventors: Golnaz Alipour Kivi, San Diego, CA (US); Soheil Ghiasihafezi, Davis, CA (US)

(73) Assignee: Storx Technologies, Inc., Davis, CA (US)

( * ) Notice: Subject to any disclaimer, the term of this patent is extended or adjusted under 35 U.S.C. 154(b) by 183 days.

(21) Appl. No.: 17/104,654

(22) Filed: Nov. 25, 2020

(65) Prior Publication Data

US 2021/0153790 A1     May 27, 2021

Related U.S. Application Data

(60) Provisional application No. 62/941,525, filed on Nov. 27, 2019.

(51) Int. Cl.
*A61B 5/145* (2006.01)
*A61B 5/00* (2006.01)
(Continued)

(52) U.S. Cl.
CPC ........ *A61B 5/14542* (2013.01); *A61B 5/0064* (2013.01); *A61B 5/01* (2013.01);
(Continued)

(58) Field of Classification Search
CPC ..... A61B 5/14542; A61B 5/0064; A61B 5/01; A61B 5/02411; A61B 5/4362;
(Continued)

(56) References Cited

U.S. PATENT DOCUMENTS 6,356,774 B1 * 3/2002 Bernstein ............. A61B 5/1495
600/323
7,047,055 B2    5/2006 Boas
(Continued)

FOREIGN PATENT DOCUMENTS

WO     2014026200 A1    2/2014

OTHER PUBLICATIONS

Regine Choe et al.; "Transabdominal near infrared oximetry of hypoxic stress in fetal sheep brain in utero"; PNAS; Oct. 28, 2003; pp. 12950-12954; vol. 100, No. 22; The National Academy of Sciences of the USA.
(Continued)

*Primary Examiner* — Eric F Winakur
*Assistant Examiner* — Abid A Mustansir
(74) *Attorney, Agent, or Firm* — NovoTechIP International PLLC

(57) ABSTRACT

Systems and methods are described, and one method includes determining a fetal blood oxygenation level, including: activating at least one light source with at least two distinct wavelengths of light on an abdomen of a pregnant mammal to direct light into a maternal abdomen toward a fetus; receiving a set of mixed signals from a set of photodetectors positioned at different locations on the maternal abdomen from reflected light that traverses maternal tissue or maternal tissue and fetal tissue; determining the fetal blood oxygenation level by performing computations on a composite fetal signal produced from the mixed signals; and ensuring a skin temperature of the maternal abdomen does not rise to unsafe levels due to activating the at least one light source.

17 Claims, 11 Drawing Sheets

(51) Int. Cl.
*A61B 5/024* (2006.01)
*A61B 5/01* (2006.01)

(52) U.S. Cl.
CPC ........ *A61B 5/02411* (2013.01); *A61B 5/4362* (2013.01); *A61B 5/6823* (2013.01); *A61B 5/725* (2013.01); *A61B 2562/0271* (2013.01)

(58) Field of Classification Search
CPC ................. A61B 5/6823; A61B 5/725; A61B 2562/0271; A61B 5/721; A61B 5/14552; A61B 5/14551; A61B 5/024; A61B 5/4356; A61B 5/7221; A61B 5/1464
See application file for complete search history.

(56) References Cited

U.S. PATENT DOCUMENTS

| | | | |
|---|---|---|---|
| 9,757,058 | B2 | 9/2017 | Ray |
| 9,968,286 | B2 | 5/2018 | Ray |
| 10,362,974 | B2 | 7/2019 | Ray |
| 2004/0034294 | A1 | 2/2004 | Kimball |
| 2005/0038344 | A1 | 2/2005 | Chance |
| 2010/0030041 | A1* | 2/2010 | Bruinsma .......... A61B 5/14552 600/322 |
| 2018/0070871 | A1 | 3/2018 | Ray |
| 2018/0296156 | A1 | 10/2018 | Penders |
| 2019/0343437 | A1 | 11/2019 | Ray |
| 2020/0214603 | A1 | 7/2020 | Ghiasi et al. |
| 2020/0245879 | A1 | 8/2020 | Ghiasi et al. |
| 2022/0361774 | A1* | 11/2022 | Ray ..................... A61B 5/1464 |

OTHER PUBLICATIONS

Daniel D. Fong et al.; "Contextually-aware Fetal Sensing in Transabdominal Fetal Pulse Oximetry"; 2020 ACM/IEEE 11th International Conference on Cyber-Physical Systems (ICCPS) Sydney, NSW, Australia; 2020; pp. 119-128; IEEE.

Daniel D. Fong et al.; "Design and In Vivo Evaluation of a Non-Invasive Transabdominal Fetal Pulse Oximeter"; IEEE Transactions on Biomedical Engineering; Jan. 2021; pp. 256-266; vol. 68, No. 1; IEEE.

Shoko, Nioka et al.; "Fetal transabdominal pulse oximeter studies using a hypoxic sheep model"; The Journal of Maternal-Fetal and Neonatal Medicine; Jun. 2005; pp. 393-399; vol. 17, No. 6; Taylor & Francis Group Ltd.

Anna Zourabian et al.; "Trans-abdominal monitoring of fetal arterial blood oxygenation using pulse oximetry"; Journal of Biomedical Optics; Oct. 2000; pp. 391-405; vol. 5, No. 4; Society of Photo-Optical Instrumentation Engineers.

International Search Report and Written Opinion dated Mar. 19, 2021 in PCT/US2020/062474.

Sugiura, "Photothermal therapy of tumors in lymph nodes using gold nanorods and near-infrared laser light with controlled surface cooling," Nano Research, Tsinghua University Press, CN, vol. 8, No. 12, Oct. 17, 2015 (Oct. 17, 2015), pp. 3842-3852.

* cited by examiner

| Fetal Health Indicator (Where Confidence Indicator Is Strong) | | | |
|---|---|---|---|
| Estimated FSpO2 | Category I | Category II | Category III |
| Sufficient Oxygenation | Green | Green | Orange |
| Insufficient Oxygenation | Orange | Red | Red |

FIG. 8A

| Fetal Health Indicator (Where Confidence Indicator Is Weak) | | | |
|---|---|---|---|
| Estimated FSpO2 | Category I | Category II | Category III |
| Sufficient Oxygenation | Green | Orange | Red |
| Insufficient Oxygenation | Green | Orange | Red |

FIG. 8B

SAFE AND RELIABLE TRANSABDOMINAL FETAL OXIMETRY

This application claims the benefit of priority from U.S. Provisional Patent Application Ser. No. 62/941,525 filed Nov. 27, 2019, and entitled "SAFE AND RELIABLE TRANSABDOMINAL FETAL OXIMETRY", which is incorporated by reference herein in its entirety.

STATEMENT AS TO RIGHTS TO INVENTIONS MADE UNDER FEDERALLY SPONSORED RESEARCH AND DEVELOPMENT

This invention was made with Government support under Grant Nos. 1838939 and 2015174, awarded by the National Science Foundation. The Government has certain rights in the invention.

BACKGROUND

It is common for intrapartum fetal health monitoring to use cardiotocography (CTG) machines, aka electronic fetal monitors (EFM), to jointly monitor fetal heart and uterine contractions during labor. A recent improvement for fetal health monitoring provides transabdominal (through the maternal abdomen) measurement of fetus blood oxygen saturation level referred to herein as transabdominal fetal oximetry (TFO), also sometimes referred to as transabdominal fetal pulse oximetry. Transabdominal fetal oximetry (TFO) can potentially improve fetal outcomes by providing physicians with a more objective metric of fetal well-being, namely fetal oxygen saturation. TFO technology involves shining near infrared light at several specific wavelengths into the maternal abdomen with an optical probe placed on the maternal abdomen, followed by sensing the diffused scattered light. Variations in the diffused light intensity signal are caused by physiological differences in tissue composition. The variations in the scattered light are analyzed to separate fetal information from the raw sensed mixed signal (mixture of maternal and fetal information). A pulse oximetry computation is performed on the isolated fetal signal to estimate the fetal oxygen saturation.

SUMMARY

An important consideration for TFO is to acquire a stronger signal relative to noise, which requires emitting more and more light into the body of a pregnant woman. Emitting more light must be balanced with patient safety (rise in the temperature of the mother's abdominal skin). The disclosure herein provides systems and methods for striking a balance between these two competing requirements to ensure safe operation of the TFO for intrapartum fetal health monitoring.

A method is disclosed which includes determining a fetal blood oxygenation level, comprising: activating at least one light source with at least two distinct wavelengths of light on an abdomen of a pregnant mammal to direct light into a maternal abdomen toward a fetus; receiving a set of mixed signals from a set of photodetectors positioned at different locations on the maternal abdomen from reflected light that traverses maternal tissue or maternal and fetal tissue; determining the fetal blood oxygenation level by performing computations on a composite fetal signal produced from the mixed signals; and ensuring a skin temperature of the maternal abdomen does not rise to unsafe levels due to the activation of the at least one light source.

A system is disclosed for safely determining a fetal blood oxygenation level which includes: at least one light source for positioning on a maternal abdomen of a pregnant mammal to direct light in at least two distinct wavelengths into the maternal abdomen toward a fetus; a controller to selectively activate the at least one light source; a set of photodetectors, wherein each photodetector in the set of photodetectors is positioned at a different location on the maternal abdomen to receive diffuse reflected light that traverses maternal tissue or maternal and fetal tissue to produce a set of mixed signals; a processing mechanism that receives the set of mixed signals and performs a filtering operation to produce a composite fetal signal from the set of mixed signals and determines the fetal blood oxygenation level from the composite fetal signal; and wherein the system ensures a skin temperature of the maternal abdomen does not rise to unsafe levels due to activation of the at least one light source.

A system is disclosed for safely determining fetal health which includes: at least one light source on a probe for positioning on a maternal abdomen of a pregnant mammal to direct light in at least two distinctive wavelengths into the maternal abdomen toward a fetus, wherein the probe includes a temperature sensor that provides a measurement of the skin temperature of the maternal abdomen; a motion sensor on the probe for detecting motion of the probe to allow motion of the probe to be monitored and used to determine signal quality; a controller to selectively activate the at least one light source; a set of photodetectors in the probe, wherein each photodetector in the set of photodetectors is positioned at a different location on the maternal abdomen to receive diffuse reflected light that traverses maternal tissue or maternal and fetal tissue to produce a set of mixed signals; a processing mechanism that receives the set of mixed signals and performs a filtering operation to produce a composite fetal signal from the set of mixed signals and determining the fetal blood oxygenation level from the composite fetal signal; an electronic fetal monitor that provides maternal heart rate, fetal heart rate, and uterine contraction signals that are used by the processing mechanism to present a unified indication of fetal health, wherein the unified indication of fetal health includes normal, indeterminate and abnormal fetal health, based on integration of fetal heart rate tracing and whether the estimated fetal blood oxygenation level indicates sufficient oxygenation or insufficient oxygenation; and wherein the system ensures a skin temperature of the maternal abdomen does not rise to unsafe levels due to activation of the at least one light source by adaptively reducing a duty cycle of the at least one light source. In some embodiments, methods and systems described herein ensure that the skin of the maternal abdomen remains at or below about 44, 43, 42, 41 or 40 degrees Celsius.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The figures depict one or more implementations in accord with the present teachings, by way of example only, not by way of limitation. In the figures, like reference numerals refer to the same or similar elements.

FIG. 8A illustrates an example implementation of fetal heart tracing of the IIFM in FIG. 3.

FIG. 8B illustrates another example implementation of fetal heart tracing of the IIFM in FIG. 3.

DETAILED DESCRIPTION

Figure 1:
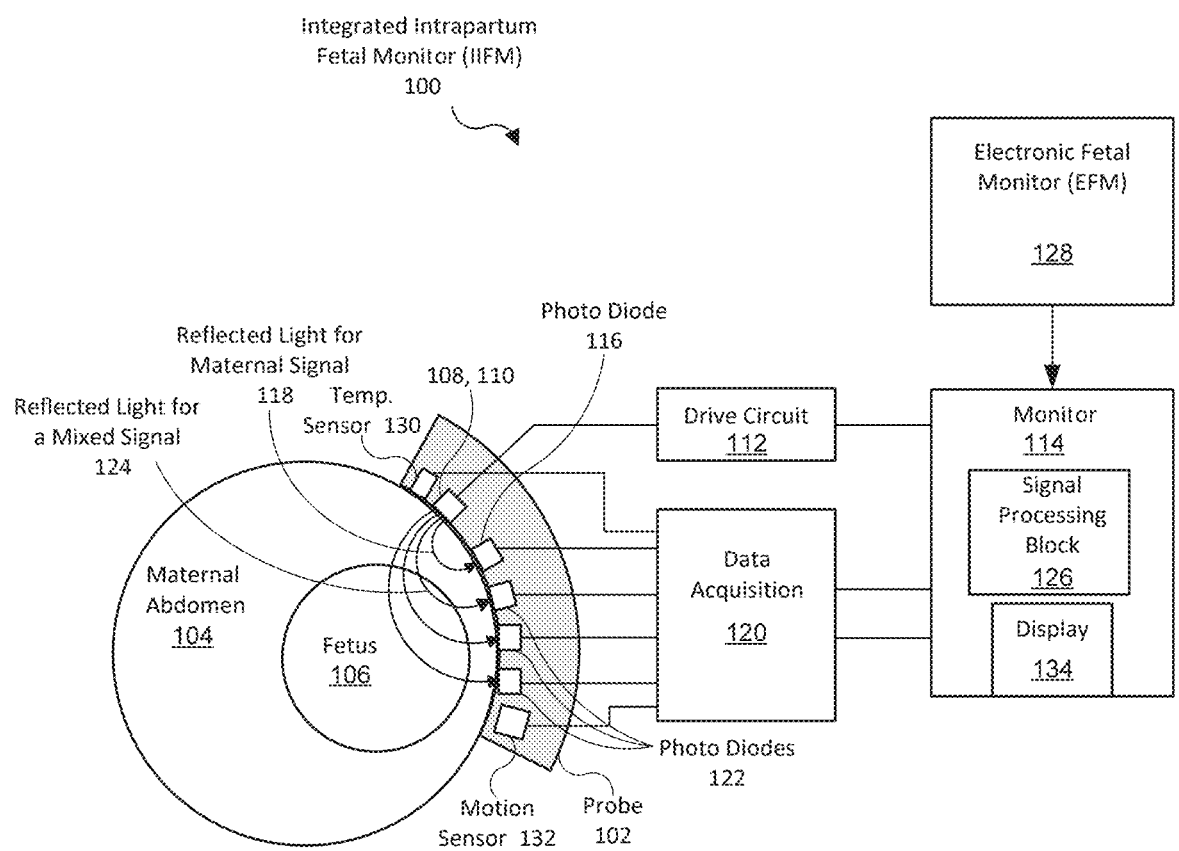
FIG. 1 illustrates a high-level diagram of an Integrated Intrapartum Fetal Monitor (IIFM) for estimating and monitoring fetal blood oxygen levels.

In the following detailed description, numerous specific details are set forth by way of examples to provide a thorough understanding of the relevant teachings. However, it should be apparent that the present subject matter may be practiced without such details. In other instances, well-known methods, procedures, components, and/or circuitry are described at a relatively high-level, without detail, to avoid unnecessarily obscuring aspects of the disclosed subject matter.

While the examples and language used focuses on a human female as the maternal abdomen, as used herein, the maternal abdomen may be any mammal. The terms fetus blood oxygenation level, fetus blood oxygen saturation level and fetus hemoglobin oxygen saturation level are used interchangeably in this document.

Safety Considerations and Applicable Standards

The safety of emitted near infrared (NIR) light by medical devices with respect to eye exposure and skin injury are evaluated using two international standards IEC 60601-2-57 and IEC 62471, respectively. Both documents are accepted by the Food and Drug Administration as Recognized Consensus Standards. IEC 60601-2-57:2012 offers specific requirements for the basic safety and essential performance of non-laser light source equipment used in medical devices. It outlines potential ocular hazards that can occur; and suggests exposure limits to protect against these hazards. It also presents a risk group classification scheme for the associated device depending on the degree to which ocular hazards are present. These limits were designed to protect patients, physicians, and other healthcare staff members from over-exposure (intentional or accidental) using worst-case scenarios, which provide a conservative safety limit. Calculated exposure limits for each ocular hazard according to IEC 60601-2-57, were compared with the emitted light energy of a device implementing the instant application. The device was below the three exposure limits, and it would be classified within the safest risk group for devices, referred to as the Exempt Group. Note that non-coherent light, unlike laser, diverges in all directions and only a very small fraction of the emitted light energy reaches the eye of an observer.

Potential skin injury due to the thermal effects from infrared optical radiation was discovered to be an important consideration for TFO. The international standard IEC 62471:2006 provides guidance to manufacturers of light-based systems on the evaluation and control of photobiological hazards and suggests a thermal hazard exposure limit for the skin. The limits are based on skin injury due to increases in tissue temperature. The maximum safe skin temperature for long term monitoring is generally thought to be about 42-44 degrees Celsius. Reducing the energy generated for continuous TFO monitoring can be accomplished by lowering the light source duty cycle as described further below. The duty cycle referred to herein is the percentage of time in which the light sources are on, as they are quickly turned on and off). Reducing the duty cycle can reduce the exposure to below the limit of the above standards. It is important to note that light decays exponentially with distance, and thus, the vast majority of emitted light energy is absorbed by, or scatters away in superficial layers of maternal tissue. The remaining energy, part of which is absorbed by the fetal tissue, is far below safety limits, eliminating concern about fetal safety. In fact, TFO faces the reverse challenge of too little light making it to the fetus. Thus, there is a balance between increasing the light to make sure sufficient light penetrates to the fetus, and lowering the light for safety of the mother.

This disclosure introduces an IIFM with safety improvements to insure the maternal abdominal skin temperature does not rise to unsafe levels with long term use of TFO monitoring. Some implementations may include at least one temperature sensor on the probe (in contact with the skin) to monitor skin temperature for heat mitigation and/or alarm generation purposes. Other implementations may include adaptively reducing the strength of the drive current of the light source emitters to the minimum-required levels based on the sensed signal strength, or adaptively reducing the duty cycle of the light sources to limit additional light exposure and thereby limit the skin temperature. Yet other implementations may include enhancing convection (airflow) around the light sources to remove heat, and adding flexible heat sinks in contact with the light sources or the skin to dissipate the heat away and cool the skin. Other implementations may also collect less frequent measurements (e.g., once every 20 seconds) to generate less heat.

FIG. 1 illustrates a high-level diagram of an Integrated Intrapartum Fetal Monitor (IIFM) 100 for safely monitoring fetal pulse oximetry using TFO technology. The IIFM 100 includes a probe 102. The probe 102 may be a "wearable" probe that is placed on a maternal abdomen 104 over a fetus 106. The probe 102 is connected to a monitor 114 which is typically placed at a patient's bedside to provide information for health care workers. The probe 102 includes at least one light source 108. The light source 108 may include one or more light-emitting diodes (LEDs) 110 (not shown) that emit light at one or more distinct wavelengths. A single light source may be used that generates two or more distinct near infrared wavelengths. Alternatively, multiple light sources may be used to generate the two or more distinct near infrared wavelengths. Most light sources generate light in a range of adjacent wavelengths (e.g. 800 nm to 820 nm). As used herein, distinct wavelengths are sufficiently separate in the light spectrum and not within one narrow range.

As illustrated in FIG. 1, the light source 108 with the LEDs 110 is positioned on the maternal abdomen 104 to direct light toward the fetus 106. The light source 108 is powered by a drive circuit 112, which operates under control of the functional blocks in monitor 114 and described further below. Two or more photodetectors are also positioned in the probe 102 on the maternal abdomen 104. The photodetectors typically comprise a photodiode. In this example, the photodetector 116 receives reflected light 118 that traverses only maternal tissue and in response produces a maternal signal to the data acquisition circuit 120. The remaining photodetectors 122 receive reflected light 124 that traverses both maternal and fetal tissue, and in response produces a mixed signal, which include contributions from both maternal and fetal tissue.

Referring again to FIG. 1, the photodetectors 116, 122 are connected to the data acquisition circuit 120. The data acquisition circuit may include a trans-impedance amplifier and an analog-to-digital (A/D) converter, which converts analog electrical signals from the photodetectors 116, 122 into a sequence of digital samples. These digital samples feed into the signal processing block 126 (described further below with reference to FIG. 2). The digital processing block 126 determines a composite fetal signal from mixed signals from the photodetectors. The system then performs computations on the composite fetal signal produced from the mixed signals to determine a fetal blood oxygenation level as follows. The signal processing block 126 performs a frequency domain and/or time domain filtering operation to remove maternal signal components from mixed signals to produce a corresponding set of fetal signals, which are then combined using a weighted average computation to derive a composite fetal signal. The system then performs a pulse oximetry computation on the composite fetal signal produced from the mixed signals to determine the fetal blood oxygenation level. During operation of the IIFM illustrated in FIG. 1, light sources 110 shine light through maternal tissue and onto fetus 106, which is typically located several centimeters below the skin. Arterial pulsations from the maternal and fetal heartbeats cause small changes in the tissue's light absorption, which cause slight changes in the diffuse reflectance when measured at the surface of the maternal abdomen 104. By measuring this change in the diffused light signal, oximetry calculations may be performed to estimate the fetus blood oxygenation levels.

As shown in FIG. 1, the IIFM system 100 may further include an Electronic Fetal Monitor (EFM) 128. The EFM 128 may be a system as previously known to monitor fetal conditions and uterine contractions during labor. The EFM may provide additional information to the IIFM 100 such as the fetus heartrate (FHR), the maternal respiratory rate (MRR), the maternal heartrate (MHR) and uterine contractions as described further below. The electronic fetal monitor provides maternal heart rate, fetus heart rate, uterine contraction, and possibly maternal respiratory rate, signals that are used by the processing mechanism in conjunction with fetal pulse oximetry using TFO technology to present a unified indication of fetal health.

Implementations of the probe 102 may further include one or more temperature sensors 130 and one or more motion sensors 132 as shown in FIG. 1. The temperature sensor 130 may be placed in close proximity to the light source 108 to monitor the maternal skin temperature where the temperature may be the highest. In some implementations, the temperature may be monitored via near infrared radiation of the skin using the photodetectors 116, 122. Alternatively, in other implementations the temperature may not be sensed at all, but predicted using heat dissipation models and knowledge of the generated heat. The motion sensor 132 is connected to the data acquisition circuit 120. The motion signal from the motion sensor to detect motion may then be connected to the filter generator 222 in the signal processing block as shown in FIG. 2.

Figure 10:
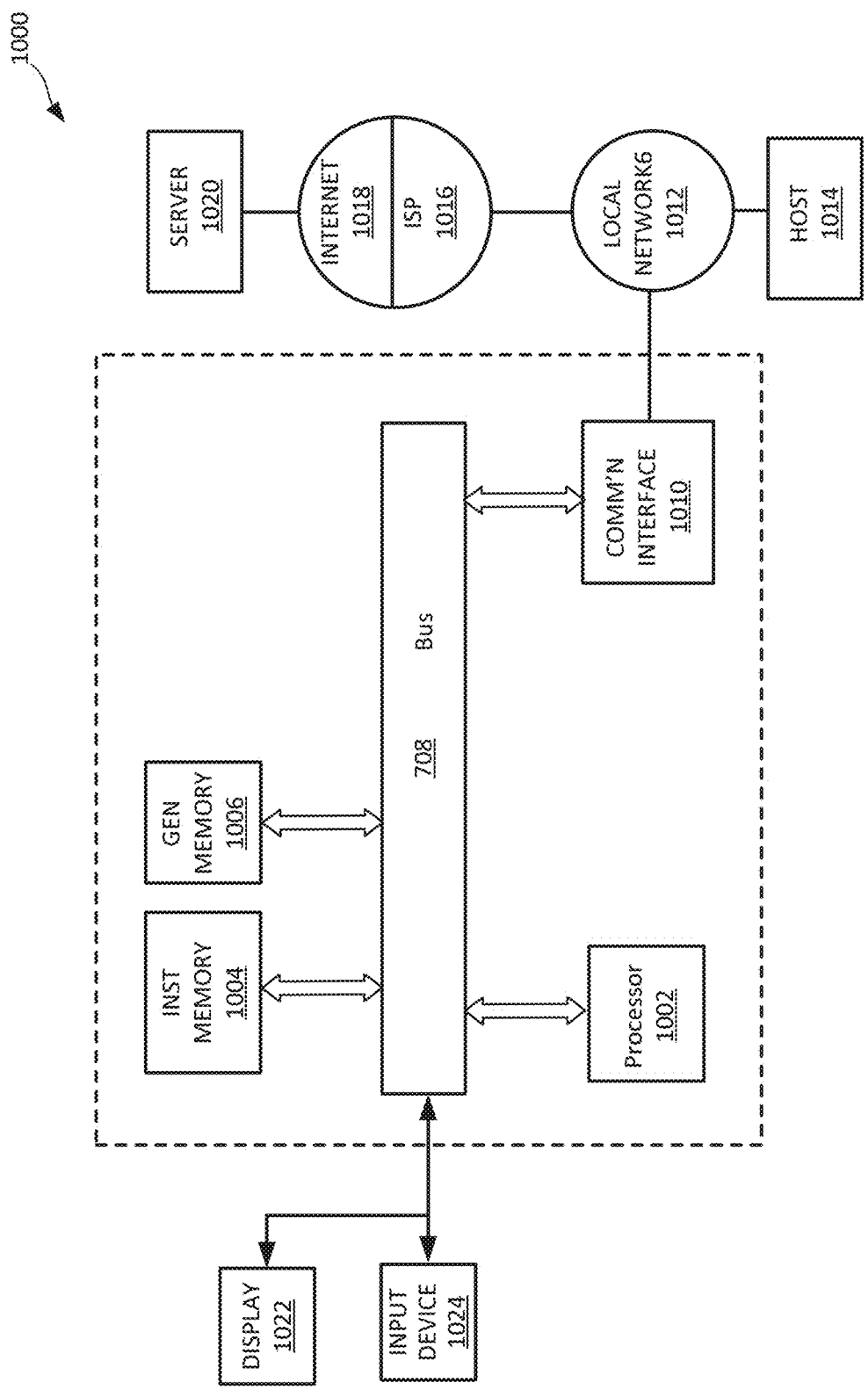
FIG. 10 illustrates a functional block diagram of an example computer system upon which aspects of this disclosure may be implemented.

It is noted that FIG. 1 is a general representation of the physical entities of the IIFM system and should not be considered to limit that actual physical arrangement of the various entities of the system. For example, the drive circuit 112 and the data acquisition circuit 120 may physically reside in the probe 102 or in the monitor 114. For purposes of this descriptions, it is assumed that the drive circuit 112 and the data acquisition circuit 120 reside in the probe 102. The monitor 114 may include a display 134 for displaying information to a user as described further below. The display 134 may also be the same display 1022 as shown in FIG. 10.

Figure 2:
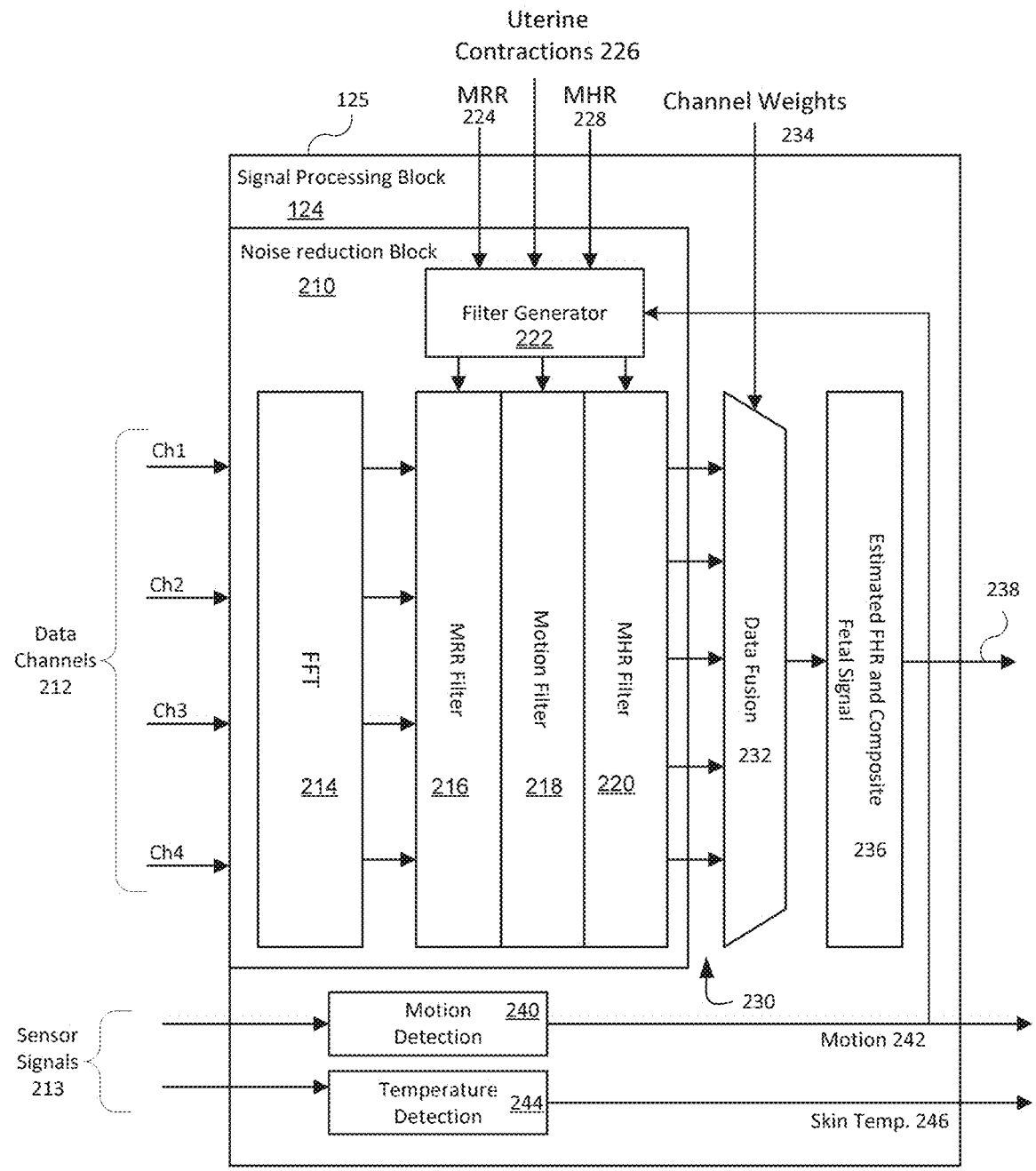
FIG. 2 illustrates a block diagram of a signal processing block of the IIFM introduced in FIG. 1.

FIG. 2 illustrates a high-level diagram of the signal processing block 124 introduced in FIG. 1. The signal processing block 124 includes a noise reduction block 210 that receives a number of data channels, collectively referred to as channels 212, from the probe 102 (shown in FIG. 1). In this example, the data channels 212 include five channels, namely channels Ch1, Ch2, Ch3, Ch4 and Ch5. Data channels Ch1, Ch2, Ch3 and Ch4 carry signals received from the photodetectors (such as photodetectors 116, 122 in FIG. 1). These signals feed into the noise reduction block 210. The noise reduction block 210 may provide filtering in frequency domain and/or the time domain. For filtering in the frequency, the data channels are input to the Fast Fourier Transform block 214. The FFT block 214 performs FFT operations on the mixed signals to compute corresponding frequency-domain representations of the mixed signals. These frequency-domain representations pass through an MRR filter 216, which removes the maternal respiration component from the signal, a motion filter 218, which removes motion noise, and an MHR filter 408, which removes the maternal heart rate component from the signal. The MRR filter 216, the motion filter 218 and MHR filter 220 are controlled by a filter generator 222, which generates the filters based on an MRR signal 224, uterine contractions signal 226 and an MHR signal 228, which are received from external sensors such as from the EFM. The Filter generator 222 may use uterine contractions, as measured by an external uterine contraction sensor, to generate a motion filter 218 that removes signal artifacts induced by the uterine contractions. The output of the photodetectors on the data channels may be directly applied to the MRR filter 216, or other filters, for filtering in the time domain.

Referring again to FIG. 2, the resulting filtered signals 230 from the noise reduction block 210 feed through a data fusion component 232. The data fusion component 232 computes a weighted average of the filtered signals based on a set of dynamically changing channel weights 234, to produce an estimated FHR and a composite fetal signal 236. Although it is possible to use a weighted average function to compute the estimated FHR and the composite fetal signal 234, the system is not limited to using such a weighted average. In general, other types of data fusion functions can be used. The estimated FHR and composite fetal signal 236 is output 238 from the signal processing block 124 and used as described below. The dynamically changing channel weights 234 are produced by considering the prominence of FHR and its harmonics in the spectrum of the filtered signals 230, where a channel with higher signal energy at the frequency components corresponding to the FHR and its harmonics will be assigned a higher channel weight. Channel weights are dynamically adjusted as new data samples stream through the system.

The signal processing block 126 in FIG. 2 may further include a motion detection block 240 that produces a motion signal 242 and a temperature detection block 244 that produces a skin temperature signal 246. The motion detection block 240 may use an input signal 213 from one or more motion sensors 132 in the probe 102. The system may determine movement of the probe and produce the motion signal 242. The motion signal 242 is sent to the filter generator 222 to remove noise caused by the motion. Further, the temperature detection block 244 may input a signal 213 from the temperature sensor 130 that directly measures the temperature of the skin under the probe 102. Motion and temperature may also be estimated from data on the data channels 212 from the photo detectors. For example, skin temperature may be sensed via near infrared radiation of the skin using the photodetectors 116, 122 using existing techniques to process data received from the photodetectors over data channels 212.

Figure 3:
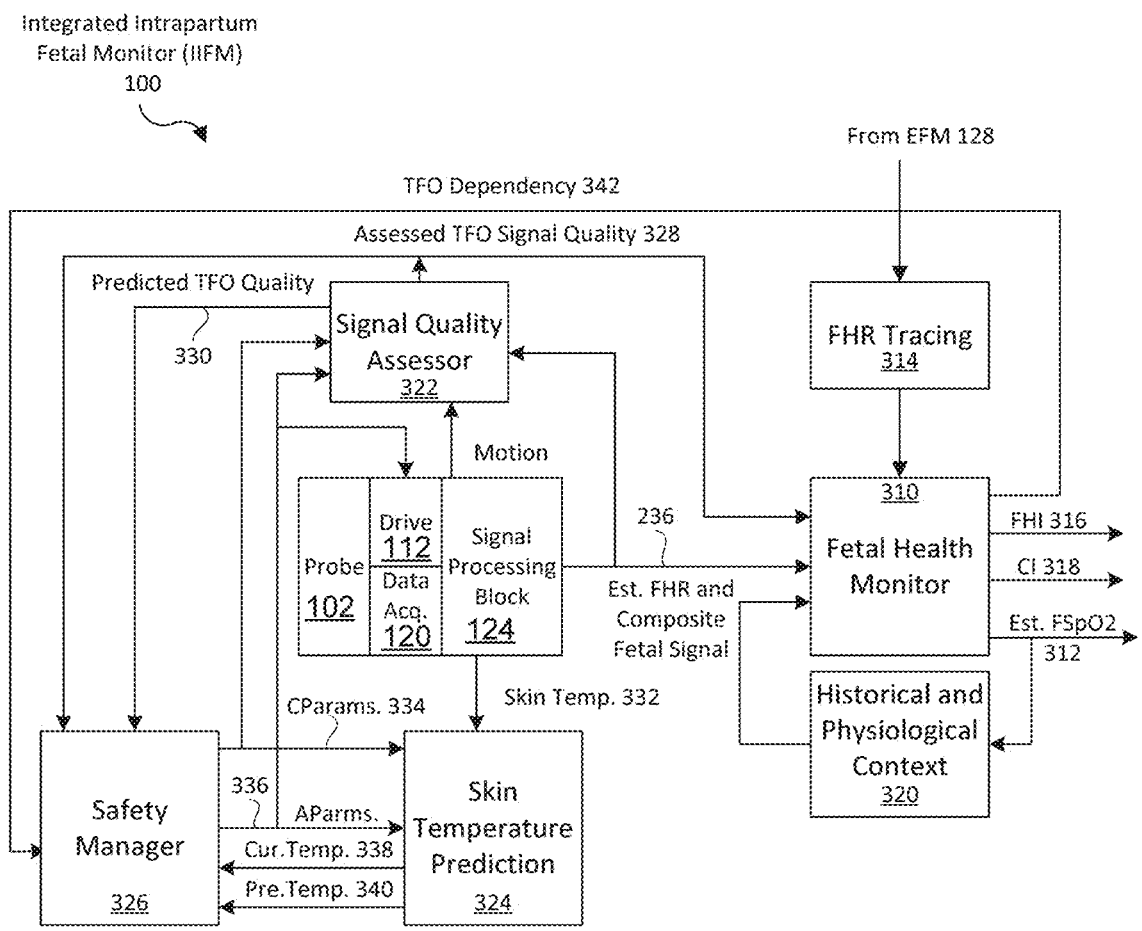
FIG. 3 illustrates a functional block diagram of the IIFM introduced in FIG. 1.

FIG. 3 illustrates a high-level diagram of the IIFM 100 as introduced in FIG. 1. FIG. 3 provides a block diagram of the various functional blocks of the IIFM 100 including the functions of the monitor 114. FIG. 3 is not meant to indicate or limit the actual physical location of the described entities. The IIFM 100 uses input from the probe 102 and the EFM 128 to safely estimate the fetus blood oxygenation levels as described herein. The IIFM 100 includes the signal processing block 124 described in FIG. 2. The signal processing block 126 inputs signals from the probe 102 via the data acquisition circuit 120 as described above. The signal processing block 126 outputs the estimated FHR and composite fetal signal 236 as described above. The estimated FHR and composite fetal signal 236 feeds into a fetal health monitor 310. Implementations of the system may include a fetal heart rate tracing module 314, which uses standard fetal heart rate tracing techniques, to generate a separate indicator for the oxygenation of the fetus. Implementations may also include a historical and physiological context module 320, a signal quality assessor 322, a skin temperature prediction module 324 and a safety manager 326. These various modules and entities are described further below.

The fetal health monitor 310 receives the estimated FHR signal 236 and analyzes the energy of the estimated FHR signal 236 at the FHR frequency to compute an estimated fetal blood oxygenation level 312 using a wavelength-ratio-based technique for computing blood oxygenation. The fetal health monitor 310 may also receive input from the historical and physiological context module 320 and an assessed TFO signal quality signal 328 from the signal quality assessor 322. The fetal health monitor 310 further outputs a fetal health indicator 316 and a confidence indicator 318 as described further below. The fetal health indicator 316 indicates the level of risk for fetal hypoxia. The confidence indicator 318 indicates the level of confidence of the device in its assessment of fetal health. Note that the system can use an FHR obtained through an external FHR sensor or an estimated FHR to determine the estimated fetal blood oxygenation level (Estimated FSpO2) 312.

The fetal heart rate tracing module 314 produces a separate indicator of the oxygenation level of the fetus (sufficiently oxygenated, indeterminate, insufficiently oxygenated) based on the FHR obtained through an external FHR sensor such as from the EFM 128. Fetal heart rate tracing module 314 also interprets FHR in the context of uterine contractions obtained through the external uterine contraction sensor also in the EFM 128. The system can use this separate indicator as an additional factor while determining the blood oxygenation level of the fetus. This alternatively generated estimate can be used as a "sanity check" for the estimate produced using the estimated FHR and composite fetal signal from the signal processing block.

The IIFM 100 also includes a historical and physiological context module 320. The historical and physiological context module 320 prevents changes in the estimated fetal blood oxygenation level that are deemed unlikely due to conflict with prior measurements or the physiological context. The historical and physiological context module 320 uses a piece wise-linear representation for previously determined fetal blood oxygenation levels to compute an upper bound on how quickly blood oxygenation levels can change. The bound is further refined by incorporating physiologically-plausible rate of oxygen exchange between the fetus and mother. If a rate of change associated with a currently determined fetal blood oxygenation level exceeds the upper bound, the system caps the currently determined fetal blood oxygenation level based on the upper bound. Note that the output from historical and physiological context module 320 can feed into fetal health monitor 310 to provide yet another sanity check.

Referring again to FIG. 3, some implementations of the IIFM 100 include a signal quality assessor 322 as shown in FIG. 3. The signal quality assessor 322 quantifies the quality of the acquired fetal signals (sometimes called photo-plethysmograph (PPG) waveforms) represented in the composite fetal signal 236. The signal quality assessor 322 receives input from the signal processing block 124 and the safety manager 326 to output an assessed TFO signal quality 328 and a predicted TFO quality 330.

Other implementations of the IIFM 100 also include a skin temperature prediction module 324 as shown in FIG. 3. The skin temperature prediction module 324 may receive a skin temperature 332 from the signal processing block 124, and candidate parameters 334 and applied parameters 336 from the safety manager to provide a current temperature 338 and a predicted temperature 340 to the safety manager 326.

Implementations of the IIFM 100 also include a safety manager 326 as shown in FIG. 3. The safety manager 326 receives the current temperature 338 and a predicted temperature 340 from the safety manager 326. It also receives the assessed TFO signal quality 328 and the predicted TFO quality 330 from the signal quality assessor 322, and the TFO dependency signal 342 from the fetal health monitor 320. The safety manager 326 periodically (at a time period "T") configures the TFO system applied parameters 336 to balance safety constraints and signal acquisition needs. The safety manager performs at least three basic functions. First, if FSpO2 does not strongly depend on TFO (FHR tracing outputs category I or category III as described below), the safety manager defers collection of TFO measurements. Second, if FSpO2 strongly depends on TFO (FHR tracing outputs category II), the safety manager 326 balances acquisition of high-quality TFO with safe temperature rise of skin of the maternal abdomen. The safety manager balances quality signal acquisition with safe temperature rise via controlling the applied parameters to the light source consisting of the drive current, the duty cycle, and TFO measurement scheduling (e.g., 1 second ON and 9 seconds OFF). To ensure Safety, if the skin temperature is projected to reach unsafe levels the safety manager 326 turns off TFO and may also generate an alarm for an operator. Third, the safety manager 326 provides candidate configuration parameters 334 and applied configuration parameters to the various blocks of the IIFM. The applied configuration parameters are provided to the drive circuit 112 to drive the light source 108. A detailed implementation of the safety manager is described below with reference to FIG. 9.

Figure 4A:
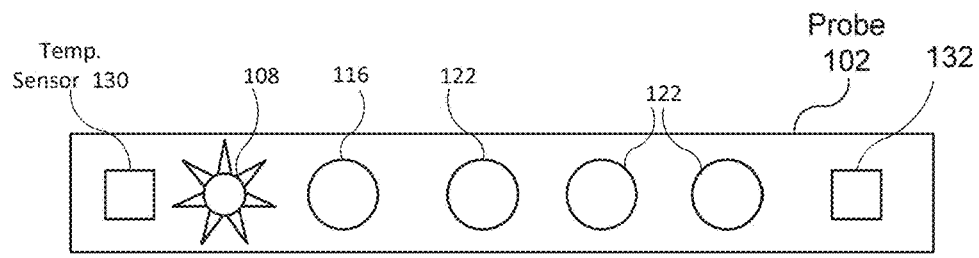
FIG. 4A illustrates a bottom view of an implementation of a probe for estimating and monitoring fetal blood oxygen levels.
Figure 4B:
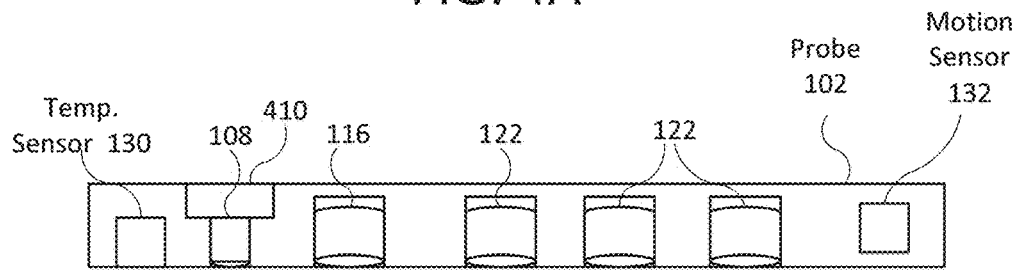
FIG. 4B illustrates a cross-sectional side view of an implementation of a probe for estimating and monitoring fetal blood oxygen levels.

FIGS. 4A-4E illustrate various views of the probe 102 introduced in FIG. 1. FIG. 4A illustrates a bottom view of an implementation of a probe 102 for estimating and monitoring fetal blood oxygen levels. In this implementation, the probe 102 includes a temperature sensor 130 in close proximity to the light source 108. The light source 108 is shown with a "star" shape around the light source 108 to graphically indicate the light source emits light. The probe 102 further includes a photodetector 116 as a light sensor that is closer to the light source 108. Other photodetectors 122 are located further away from the light source 108. The probe 102 may further include a motion sensor 132. FIG. 4B illustrates a cross-sectional side view of the probe 102 shown in FIG. 4A. In this view a heatsink 410 can be seen as described further below.

Figure 4C:
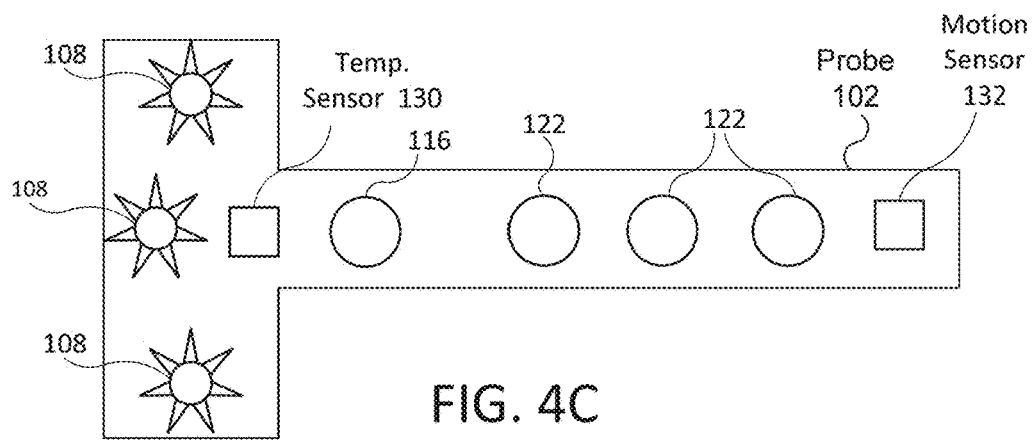
FIG. 4C illustrates a bottom view of another implementation of a probe for estimating and monitoring fetal blood oxygen levels.

FIG. 4C illustrates a bottom view of another implementation of a probe for estimating and monitoring fetal blood oxygen levels. This implementation has three light sources 108 for emitting light from different locations. The light sources 108 may emit light at the same or different frequencies. The light sources 108 may be positioned such that they are equally distant from one or more of the photodetectors that are further from the light source, such as photodetectors 122.

Figure 4D:
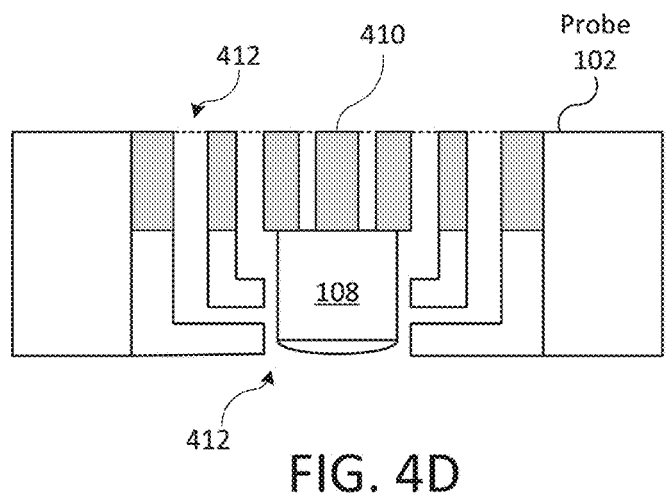
FIG. 4D illustrates an enlarged view of an implementation of a light source in a probe for estimating and monitoring fetal blood oxygen levels.

FIG. 4D shows an enlarged view of an implementation of a light source 110 in a probe 102. In this implementation, a heatsink 410 is in close proximity and may be in contact with the backside of the light source 110. This implementation further includes a number of convection and airflow channels 412 that help cool the light source and the skin in contact with the light source. The light source 108 may comprise one or more LEDs.

Figure 4E:
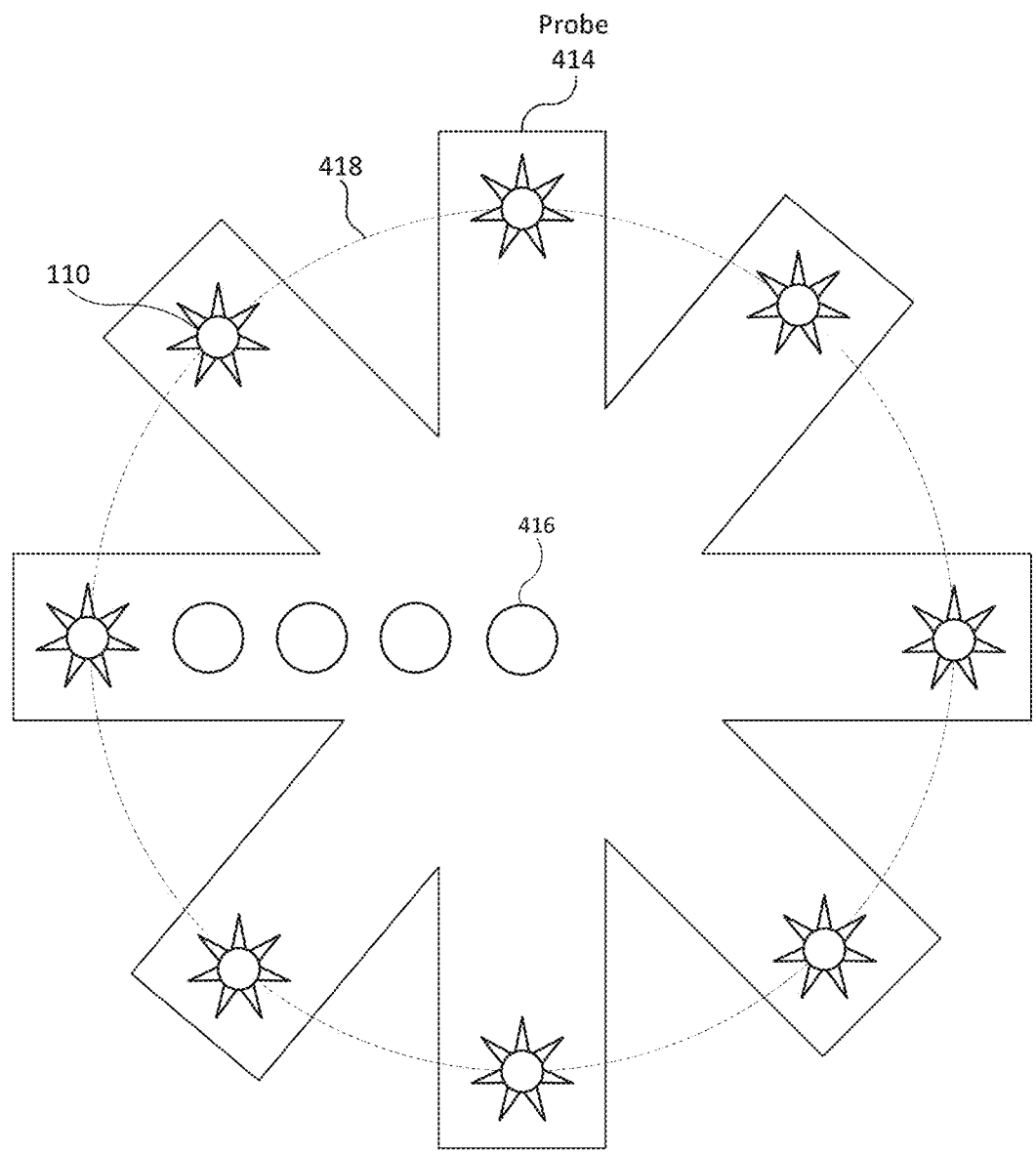
FIG. 4E illustrates a bottom view of another implementation of a probe for estimating and monitoring fetal blood oxygen levels.

FIG. 4E illustrates a bottom view of another implementation of a probe 414 for estimating and monitoring fetal blood oxygen levels. In this implementations, light sources 110 are arranged in a pattern around the photodetectors. In this example, the light sources 110 are centered equally spaced from a center photodetector 416 around a circle 418.

Figure 5:
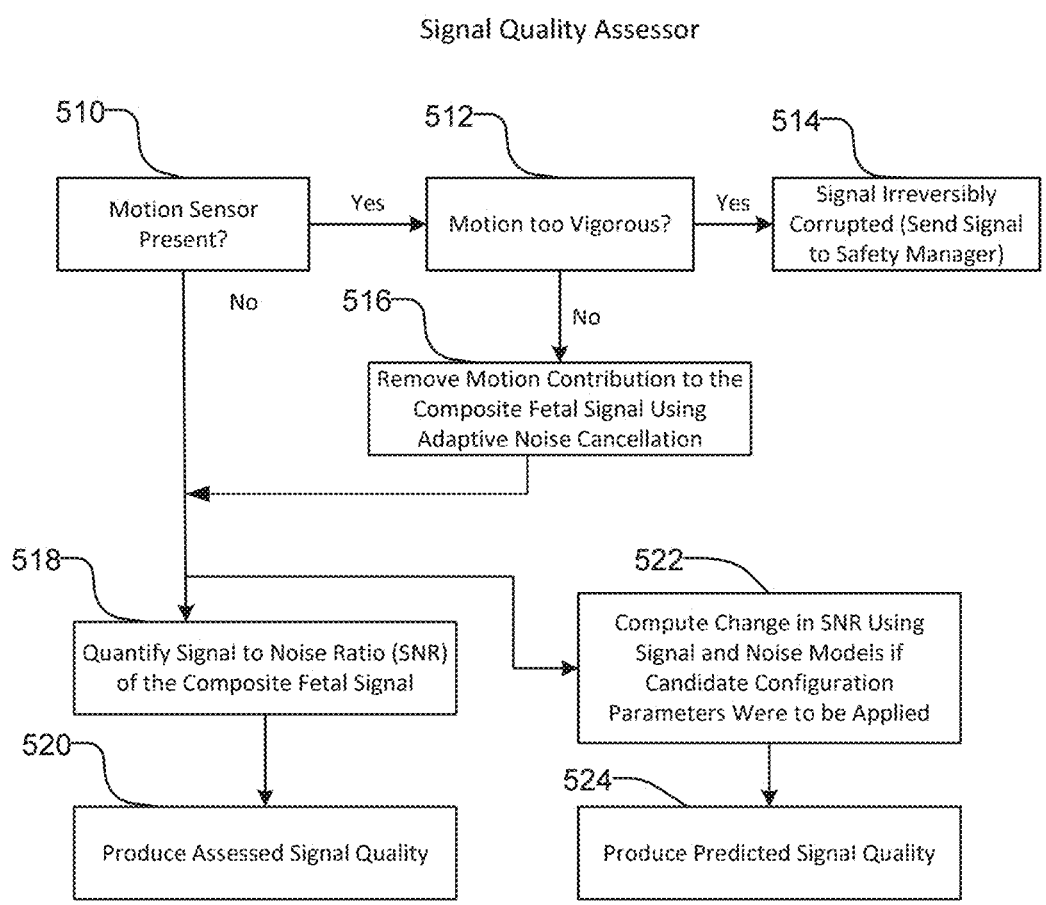
FIG. 5 illustrates a flowchart of an implementation of a signal quality assessor of the IIFM in FIG. 3.

FIG. 5 is a flowchart of an example implementation of the signal quality assessor 322 of the IIFM 100 as shown in FIG. 3. The signal quality assessor 322 quantifies the quality of the acquired fetal signals represented in the composite fetal signal 236. The signal quality assessor 322 determines if there is a motion sensor present (step 510). The motion sensor may be a dedicated motion sensor on the probe or from data received on the data channels from the photo detectors as described above. If there is a sensor present (step 510=yes) then the signal quality assessor 322 determines if the motion is too vigorous (step 512). If the motion is too vigorous (step 512=yes) then the signal is irreversibly corrupted and the signal quality assessor send a signal to the safety manager (step 514). If the motion is not too vigorous (step 512=no) then the signal quality assessor removes motion contribution to the composite fetal signal using adaptive noise cancellation (step 516) and proceeds to step 518. Removing the motion contribution to the composite fetal signal using adaptive noise cancellation may include adjusting inputs to the motion filter 218 via the filter generator 222 described above.

Referring again to the flowchart of FIG. 5, if there is no motion sensor present (step 510=no) or after removing any motion contribution (step 516), the signal quality assessor proceeds to steps 518 and 522. At step 518, the signal quality assessor quantifies the signal to noise ratio (SNR) of the composite fetal signal. The signal quality assessor then produces an assessed signal quality (step 520). The assessed signal quality is provided to the fetal health monitor 310 and the safety manager as shown in FIG. 3. At step 522, the signal quality assessor computes change in the SNR using signal and noise models if the candidate configuration parameters were to be applied. The signal quality assessor then produces a predicted signal quality (step 524). The predicted signal quality is provided to the safety manager as shown in FIG. 3.

Figure 6:
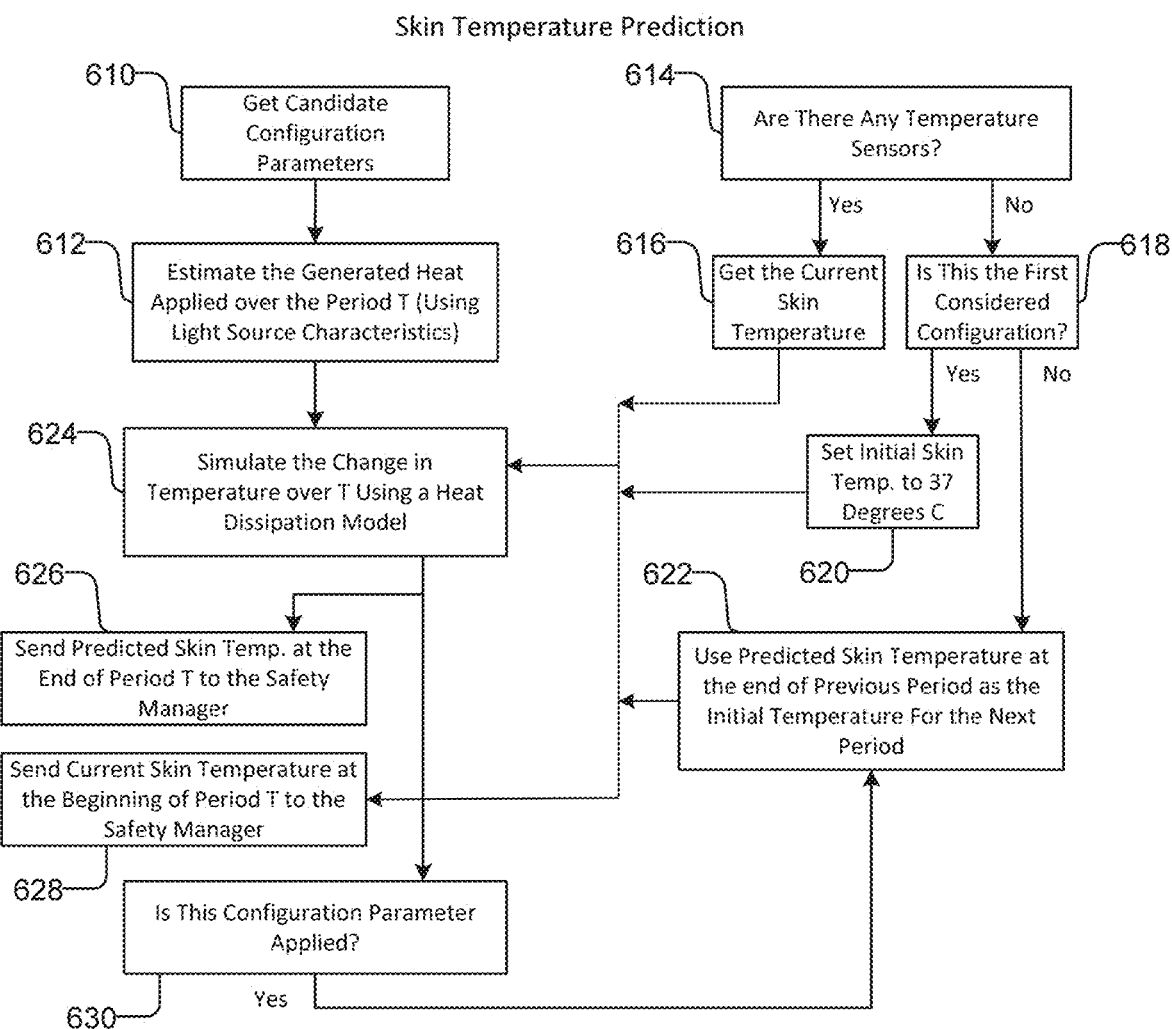
FIG. 6 illustrates a flowchart of an implementation of skin temperature prediction in the IIFM in FIG. 3.

FIG. 6 is a flowchart of an example implementation of the skin temperature prediction module 324 in the IIFM 100 as shown in FIG. 3. The skin temperature prediction module 324 begins with steps 610 and 614. The skin temperature prediction module 324 gets candidate configuration parameters (step 610) and estimates the generated heat applied over the period T using light source characteristics (step 612). Approximately concurrent to steps 610 and 612, the skin temperature prediction module 324 determines if there are any temperature sensors that provide a measured skin temperature (step 614). If there are any temperature sensors (step 614=yes) then the skin temperature prediction module 324 gets the current skin temperature (step 616). If there are no temperature sensors (step 614=no) then the skin temperature prediction module 324 determines if this is the first considered configuration (step 618). If this is the first considered configuration (step 618=yes) then the skin temperature prediction module 324 sets the initial skin temperature to 37 degrees C. (step 620). If this is not the first considered configuration (step 618=no) then the skin temperature prediction module 324 uses the predicted skin temperature at the end of the previous period as the initial temperature for the next period (step 622). The skin temperature prediction module 324 also sends the current skin temperature at the beginning of period T to the safety manager (step 628).

Referring again to the flowchart of FIG. 6, at step 624 the skin temperature prediction module 324 receive an estimate of the generated heat (from step 612) and an initial skin temperature (from step 616, step 620 or step 622) to simulate the change in temperature over period T using a heat dissipation model. The skin temperature prediction module 324 then sends a predicted skin temperature at the end of a period T to the safety manager (step 626). The safety manager 326 uses the information received from the skin temperature prediction module 324, to determine if the current candidate configuration parameters should be applied to the probe (further discussed below). Where the configuration parameters used in step 624 are applied parameters (step 630=yes) then the skin temperature prediction module 324 proceeds to step 622 to record the simulated skin temperature at the end of the current period T (derived in step 624), as the initial skin temperature at the end of the subsequent period.

Figure 7:
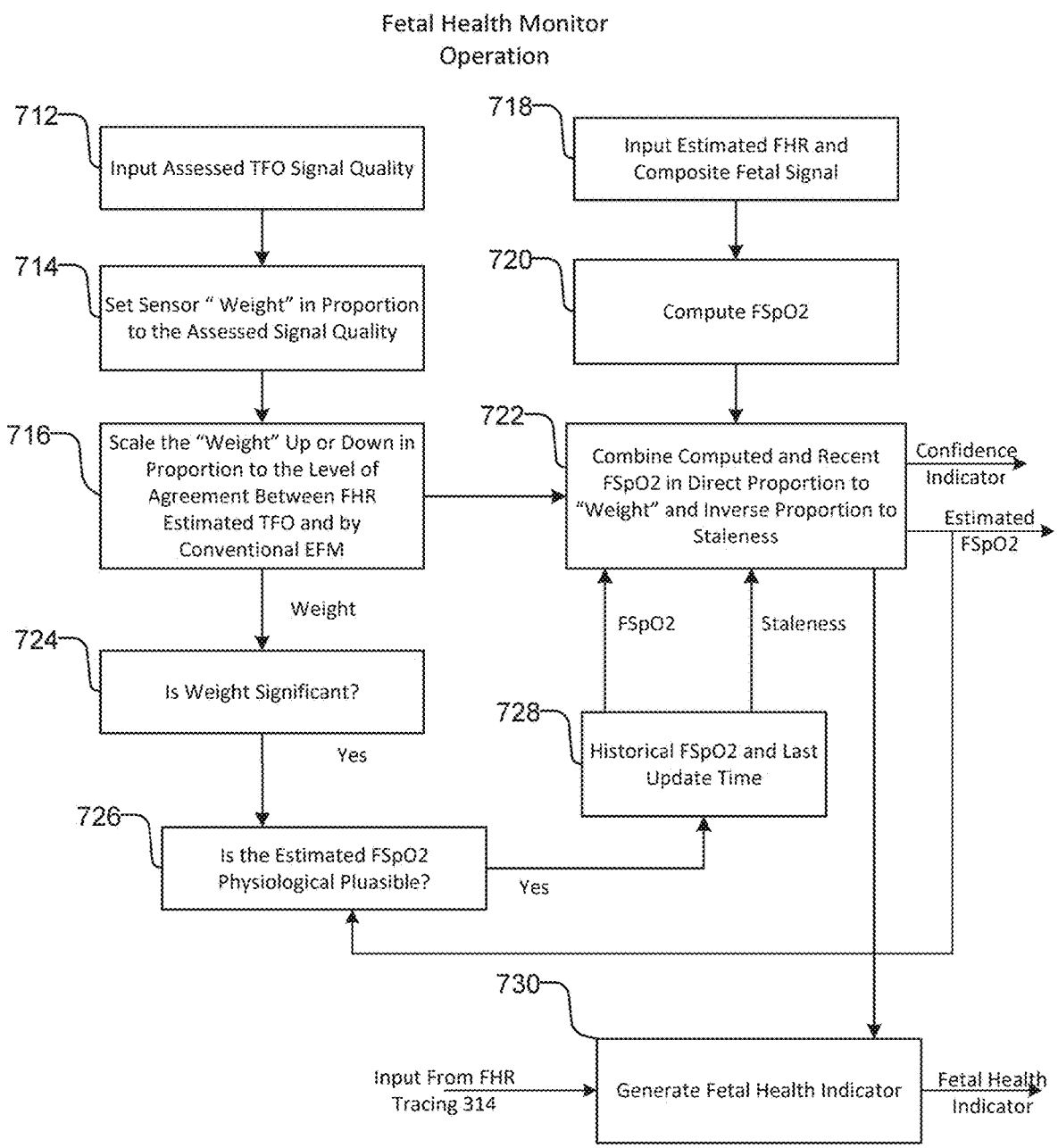
FIG. 7 illustrates a flowchart of an implementation of a fetal health monitor of the IIFM in FIG. 3.

FIG. 7 is a flowchart of an example implementation of the fetal health monitor 310 in the IIFM 100 as shown in FIG. 3. The fetal health monitor 310 begins with steps 712 and 718. The fetal health monitor 310 inputs the assessed TFO signal quality from the signal quality assessor (step 712). The fetal health monitor 310 sets the sensor weight for the composite fetal signal received from the signal processing block 124 in proportion to the assessed signal quality (step 714). Where the sensor weight models the confidence in TFO sensor. The fetal health monitor 310 then scales the "sensor weight" up or down in proportion to the level of agreement between the FHR estimated by the TFO and by the conventional EFM (step 716). The fetal health monitor 310 also inputs the estimated FHR and the composite fetal signal (step 718) and computes FSpO2 (step 720). At step 722, the fetal health monitor combines the computed FSpO2 and the recent or historical FSpO2 in direct proportion to the sensor weight and in inverse proportion to the staleness to produce the estimated FSpO2 and the confidence indicator. The fetal health monitor also generates the fetal health indicator using the estimated FSpO2 and the FHR tracing category received from the FHR tracing module 314 (step 730) as further described in reference to FIG. 8. If the weight is significant (step 724) and the estimated FSpO2 (output of 722) is physiologically plausible (step 726) the fetal health monitor proceeds to step 728 to record the estimated FSpO2 (output of 722) in historical FSpO2 and update its last update time (step 728).

FIGS. 8A and 8B represent an implementation of displaying the fetal health indicator produced by the fetal health monitor 310. In this implementation, the fetal health indicator integrates the estimated FSpO2 and the industry fetal heart rate tracing classification obtained from the EFM to present a unified indication of fetal health. The unified indication of fetal health may be presented to health professionals as shown in FIGS. 8A and 8B. The industry fetal heart rate (FHR) tracing classification provides three categories of FHR tracing. Category I FHR tracings are considered to be "normal" and are not typically associated with fetal complications. Category II FHR tracings are indeterminate. Category III FHR tracing are abnormal and have associated with adverse neurologic abnormalities. The fetal health indicator displays one of three values using the colors green, orange and red. The fetal health indicator colors are typically shown on the display 134 to health professionals. The fetal health indicator color is displayed depending on the FHR tracing category, the estimated FSpO2 value and confidence indicator from the fetal health monitor. FIG. 8A provides a table for the fetal health indicator where the confidence indicator is strong. For example, if the estimated FSpO2 shows there is sufficient oxygenation the fetal health indicator will indicate the color green if the category is I or II, and will indicate orange for category III. Similarly, FIG. 8B provides a table for the fetal health indicator where the confidence indicator is weak.

Figure 9:
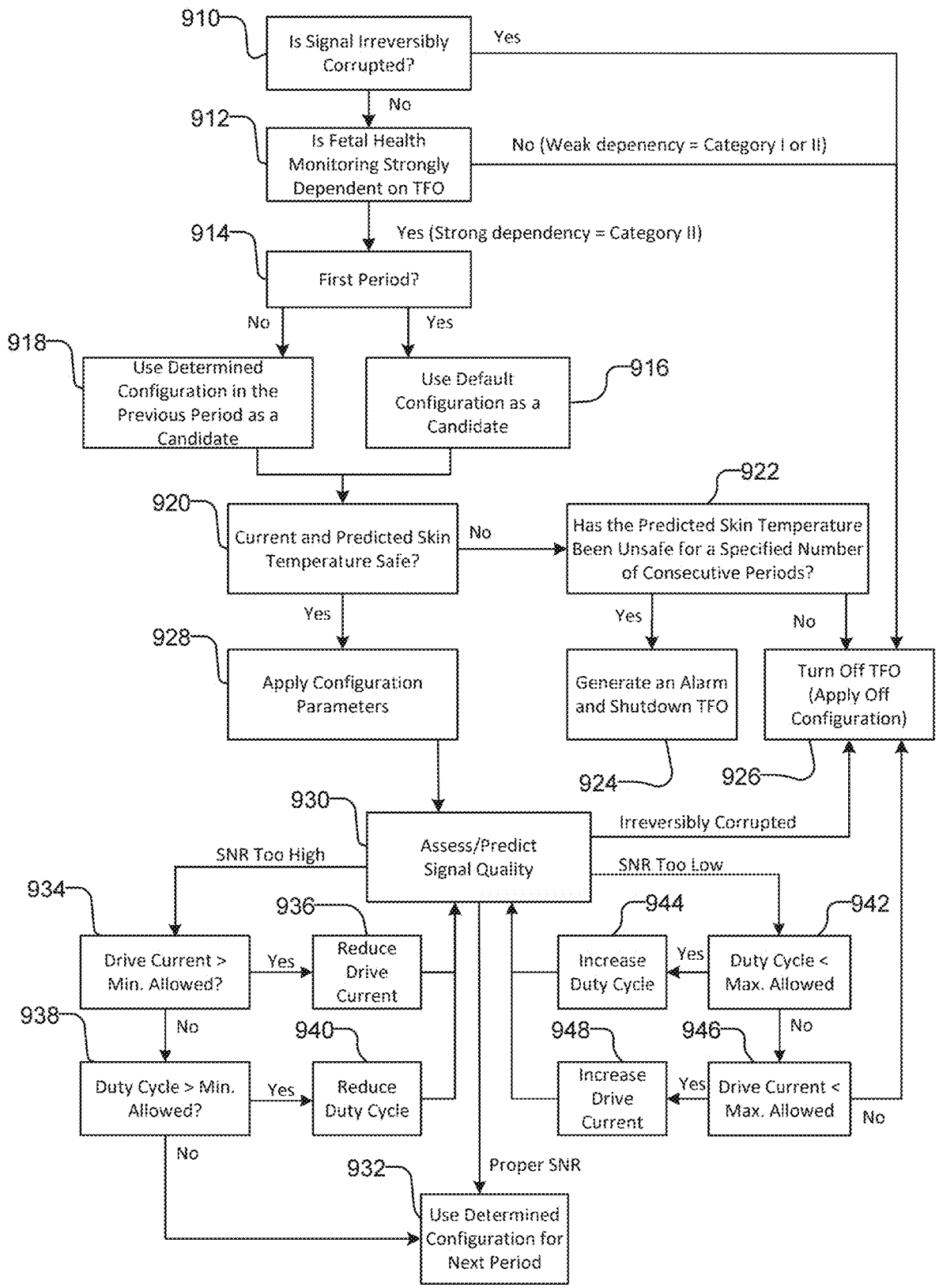
FIG. 9 illustrates a flowchart of an implementation of a safety manager of the IIFM in FIG. 3.

FIG. 9 is a flowchart of an example implementation of the safety manager 326 in the IIFM 100 as shown in FIG. 3. The safety manager 326 determines if the estimated FHR and composite fetal signal is irreversibly corrupted (step 910). If the signal is irreversibly corrupted (step 910=yes) then the safety manager 326 turns off TFO by applying an off configuration (step 926). If the signal is not irreversibly corrupted (step 910=no) then the safety manager 326 determines if fetal health monitoring is strongly dependent on TFO (step 912). As used herein, fetal health monitoring is strongly dependent on TFO when in category II and not strongly dependent on TFO when in category I or III. If the safety manager 326 determines fetal health monitoring is not strongly dependent on TFO (step 912=no) then it proceeds to step 926. If the safety manager 326 determines fetal health monitoring is strongly dependent on TFO (step 912=yes) then it determines if this is the first period (step 914). If this is the first period (step 914=yes) then the safety manger uses a default configuration as the candidate (step 916) and proceeds to step 920. If this is not the first period (step 914=no) then the safety manger uses the determined configuration in the previous period as the candidate (step 918) and proceeds to step 920. The safety manger inputs the current and predicted skin temperatures and determines if they are safe (step 920). If the skin temperature being used, current or predicted, is not safe (step 920=no) then it determines if the predicted skin temperature has been unsafe for a specified number of consecutive time periods (step 922). If the skin temperature has been unsafe for the specified number of consecutive time periods (step 922=yes) then the safety manager generates an alarm and shuts down TFO (step 924). If the skin temperature has not been unsafe for the specified number of consecutive time periods (step 922=no) then the safety manager turns off TFO by applying an off configuration (step 926).

Referring again to the flowchart in FIG. 9, if the skin temperature being used, current or predicted, is safe (step 920=yes) then the safety manager applies the configuration parameters (step 928), which may include using the parameters to drive the light source. The safety manager 326 then assesses the signal quality for the applied parameters (step 930). At step 930, the safety manager assesses applied parameters and predicts for candidate parameters the signal quality to enable the safety manager to adjust the parameters until a proper SNR is determined. Where there is a proper SNR the safety manager uses the determined configuration for the next period (step 932). If the signal quality is irreversibly corrupted, then the safety manager proceeds to step 926 to turn off TFO.

The safety manager may iteratively adjust the candidate parameters based on the SNR ratio in steps 934 to 948 to achieve a proper SNR ratio without generating excessive heat. Where the SNR is too high, the safety manager 326 determines if the drive current is greater than the minimum allowed current (step 934). If the drive current is greater than the minimum allowed current (step 934=yes) then it reduces the drive current (step 936) and returns to step 930. If the drive current is not greater than the minimum allowed current (step 934=no) then it determines if the duty cycle is greater than the minimum allowed (step 938). If the duty cycle is greater than the minimum allowed (step 938=yes) then it reduces the duty cycle (step 940) and returns to step 930. If the duty cycle is not greater than the minimum allowed (step 938=no) then it uses the determined configuration for the next period (step 932). Where the SNR is too low, the safety manager 326 determines if the duty cycle is less than the maximum allowed (step 942). If the duty cycle is less than the maximum allowed (step 942=yes) then it increases the duty cycle (step 944) and returns to step 930. If the duty cycle is not less than the maximum allowed (step 942=no) then it determines if the drive current is less than the maximum allowed (step 946). If the drive current is less than the maximum allowed (step 946=yes) then it increases the drive current (step 948) and returns to step 930. If the drive current is not less than the maximum allowed (step 946=no) then it proceeds to step 926 to turn off TFO.

FIG. 10 is a block diagram illustrating a computer system 1000. It will be understood that logic blocks illustrated in FIG. 10 represent functions, and do not necessarily correspond to particular hardware on a one-to-one basis. The computer system 1000 can include a data processor 1002, instruction memory 1004, and a general purpose memory 1006, coupled by a bus 1008. The instruction memory 1004 can include a tangible medium retrievably storing computer-readable instructions, that when executed by the data processor 1002 cause the processor to perform functions, processes, and operations according to one or more aspects of this disclosure.

The computer system 1000 can include a communications interface 1010 configured to interface with a local network 1012 for accessing a local host server 1014, and to communicate, for example, through an Internet Service Provider (ISP) 1016 to the internet 1018, and access a remote server 1020. The computer system 1000 can also include a display 1022 and a user interface or other input device 1024, either as separate devices or combined, for example, as a touchscreen display.

Those of skill in the pertinent art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Various exemplary aspects and illustrative implementations thereof are described in terms of sequences of actions performed, for example, by elements of a computing device. It will be recognized that such actions described can be performed by specific circuits (for example, application specific integrated circuits (ASICs)), by specific configurations of field programmable circuits (for example, field programmable gate arrays (FPGAs)), by program instructions being executed by one or more processors, or by a combination of both. Additionally, such sequence of actions described herein can be considered to be implemented entirely within any form of computer readable storage medium having stored therein a corresponding set of computer instructions that upon execution would cause an associated processor to perform the described herein. Thus, the various aspects of can be implemented in a number of different forms, all of which are contemplated to be within the scope of the claimed subject matter. In addition, example forms and implementations for actions and operations may be described, for example, as "logic configured to" perform the described action.

The methods, sequences and/or algorithms described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor.

Accordingly, implementations and practices according to the disclosed aspects can include a computer readable media embodying a method for de-duplication of a cache. Accordingly, the invention is not limited to illustrated examples and any means for performing the functionality described herein are included in embodiments of the invention.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein.

Language is intended and should be interpreted to be as broad as is consistent with the ordinary meaning of the language is used in the context of this disclosure, and to encompass all structural and functional equivalents. Except as stated immediately above, nothing that is stated or illustrated is intended or should be interpreted to cause dedication of any component, step, feature, object, benefit, advantage, or equivalent to the public.

It will be understood that terms and expressions used herein have the ordinary meaning accorded to such terms and expressions in their respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," and any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

In the foregoing Detailed Description, it can be seen that various features are grouped together in various examples for the purpose of streamlining the disclosure. This method of disclosure is not to be interpreted as reflecting an intention that any summary point requires more features than it expressly recites.

What is claimed is:

1. A method for safely determining a fetal blood oxygenation level, comprising:
   activating at least one light source with at least two distinct wavelengths of light on an abdomen of a pregnant mammal to direct light into a maternal abdomen toward a fetus;
   receiving a set of mixed signals from a set of photodetectors positioned at different locations on the maternal abdomen from reflected light of the at least two distinct wavelengths that traverses maternal tissue or maternal and fetal tissue;
   producing a composite fetal signal from the set of mixed signals from the set of photodetectors;
   assessing a quality of the composite fetal signal where the quality depends on a signal-to-noise ratio (SNR) of the composite fetal signal;
   determining the fetal blood oxygenation level by performing computations on the composite fetal signal produced from the mixed signals; and
   ensuring a skin temperature of the maternal abdomen does not rise to unsafe levels due to the activation of the at least one light source using the assessed quality of the composite fetal signal to determine parameters applied to the at least one light source to insure safe skin temperature levels.

2. The method of claim 1 further comprising mounting the at least one light source and the set of photodetectors in a probe fashioned for placement on the maternal abdomen of the pregnant mammal, wherein the probe incorporates convection air-flow around the at least one light source to remove heat.

3. The method of claim 1 further comprising:
   providing a motion sensor in a probe; and
   filtering the set of mixed signals received from the set of photodetectors with data from the motion sensor.

4. The method of claim 1 further comprising determining a predicted skin temperature to optimize a probe configuration.

5. The method of claim 4 further comprising predicting a signal quality of the composite fetal signal and using the predicted signal quality to set the parameters for the probe configuration.

6. The method of claim 1 wherein ensuring the skin temperature of the maternal abdomen does not rise to unsafe levels comprises adaptively reducing strength of a drive current to the at least one light source.

7. The method of claim 1 wherein ensuring the skin temperature of the maternal abdomen does not rise to unsafe levels comprises adaptively reducing a duty cycle of a drive current to the at least one light source.

8. The method of claim 1 wherein ensuring the skin temperature of the maternal abdomen does not rise to unsafe levels comprises activating the light source less frequently to determine the fetal blood oxygenation level.

9. The method of claim 1 wherein ensuring the skin temperature of the maternal abdomen does not rise to unsafe levels comprises keeping the skin temperature at or below 44, 43, 42, 41 or 40 degrees Celsius.

10. The method of claim 1 further comprising utilizing maternal heart rate, fetal heart rate, uterine contraction inputs from an electronic fetal monitor and the determined fetal blood oxygenation level to present a unified indication of fetal health and a confidence indicator.

11. The method of claim 1 further comprising:
    determining a predicted signal quality that is combined with the assessed quality of the composite signal; and
    balancing a quality signal acquisition with safe temperature rise via controlling parameters applied to the at least one light source.

12. The method of claim 1 further comprising mounting the at least one light source and the set of photodetectors in a probe fashioned for placement on the maternal abdomen of the pregnant mammal, wherein the probe provides heat sinks to dissipate heat of the at least one light source.

13. A method for safely determining a fetal blood oxygenation level, comprising:
    activating at least one light source with at least two distinct wavelengths of light in a probe on an abdomen of a pregnant mammal to direct light into a maternal abdomen toward a fetus;
    receiving a set of mixed signals from a set of photodetectors positioned at different locations on the maternal abdomen from reflected light of the at least two distinct wavelengths that traverses maternal tissue or maternal and fetal tissue;
    providing a motion sensor in the probe and filtering the set of mixed signals received from the set of photodetectors with data from the motion sensor to produce a set of motion-filtered mixed signals;
    producing a composite fetal signal from the set of motion-filtered mixed signals;
    assessing a quality of the composite fetal signal;
    determining the fetal blood oxygenation level by performing computations on the composite fetal signal produced from the mixed signals;
    and
    ensuring a skin temperature of the maternal abdomen does not rise to unsafe levels due to the activation of the at least one light source using the assessed signal quality to determine parameters applied to the at least one light source to insure safe skin temperature levels.

14. The method of claim 13 further comprising mounting the at least one light source and the set of photodetectors in a probe fashioned for placement on the maternal abdomen of the pregnant mammal, wherein the probe incorporates convection air-flow around the at least one light source to remove heat.

15. The method of claim 13 further comprising determining a predicted skin temperature to optimize a probe configuration.

16. The method of claim 15 further comprising predicting a signal quality of the composite fetal signal before a change to the probe configuration is applied.

17. The method of claim 13 further comprising:
    determining a predicted signal quality that is combined with the assessed quality of the composite signal; and
    balancing a quality signal acquisition with safe temperature rise via controlling parameters applied to the at least one light source.

* * * * *